United States Patent
Akdogan et al.

(10) Patent No.: US 9,211,498 B2
(45) Date of Patent: Dec. 15, 2015

(54) FUNCTIONAL DESICCANTS

(71) Applicant: Makefield LLC, Newtown, PA (US)

(72) Inventors: Kutadgu Akdogan, New York, NY (US); Kalyan C. Vepuri, Newtown, PA (US); Christian Von Heifner, Brooklyn, NY (US)

(73) Assignee: Makefield LLC, Newtown, PA (US)

( * ) Notice: Subject to any disclaimer, the term of this patent is extended or adjusted under 35 U.S.C. 154(b) by 69 days.

(21) Appl. No.: 14/214,442

(22) Filed: Mar. 14, 2014

(65) Prior Publication Data

US 2014/0260985 A1 Sep. 18, 2014

Related U.S. Application Data

(60) Provisional application No. 61/800,973, filed on Mar. 15, 2013.

(51) Int. Cl.
| | |
|---|---|
| *B01D 53/26* | (2006.01) |
| *B01D 53/22* | (2006.01) |
| *B01D 53/04* | (2006.01) |
| *A61J 7/02* | (2006.01) |
| *G07F 11/44* | (2006.01) |
| *A61J 7/00* | (2006.01) |
| *G07C 9/00* | (2006.01) |
| *H04N 7/18* | (2006.01) |
| *A61J 7/04* | (2006.01) |
| *G07F 9/02* | (2006.01) |
| *A61J 1/03* | (2006.01) |
| *G06F 19/00* | (2011.01) |

(52) U.S. Cl.
CPC ............. *B01D 53/261* (2013.01); *A61J 7/0076* (2013.01); *A61J 7/02* (2013.01); *A61J 7/0481* (2013.01); *G07C 9/00134* (2013.01); *G07F 9/026* (2013.01); *G07F 11/44* (2013.01); *H04N 7/188* (2013.01); *A61J 1/03* (2013.01); *B01D 53/0454* (2013.01); *G06F 19/3462* (2013.01)

(58) Field of Classification Search
CPC .. B01D 53/0454; B01D 53/22; B01D 53/229; B01D 53/261; A61J 1/03; A61J 7/0076; A61J 7/02; A61J 7/04; A61J 7/0481; A61J 7/049; H04N 7/188
USPC .................................................. 96/4; 95/117
See application file for complete search history.

(56) References Cited

U.S. PATENT DOCUMENTS

| | | |
|---|---|---|
| 4,695,954 A | 9/1987 | Rose et al. |
| 5,559,503 A | 9/1996 | Blahut |

(Continued)

FOREIGN PATENT DOCUMENTS

WO WO-2014145074 9/2014

OTHER PUBLICATIONS

"International Application Serial No. PCT/US14/29733, Search Report and Written Opinion mailed Aug. 18, 2014", 9 pages.

*Primary Examiner* — Jason M Greene
(74) *Attorney, Agent, or Firm* — Strategic Patents, P.C.

(57) ABSTRACT

A device includes a desiccant and an enclosure having an interior surrounding the desiccant. The enclosure may include a moisture vapor permeable membrane with a moisture permeability sufficient to pass moisture from outside the enclosure to the desiccant. The device may further include a functional device within the enclosure having processing circuitry to perform at least one function associated with the desiccant.

31 Claims, 3 Drawing Sheets

(56) References Cited

U.S. PATENT DOCUMENTS

| | | |
|---|---|---|
| 5,597,995 A | 1/1997 | Williams et al. |
| 6,371,297 B1 | 4/2002 | Cha |
| 6,411,567 B1 | 6/2002 | Niemiec et al. |
| 6,507,275 B2 | 1/2003 | Romano et al. |
| 6,529,801 B1 | 3/2003 | Rosenblum |
| 6,604,019 B2 | 8/2003 | Ahlin et al. |
| 6,662,081 B1 | 12/2003 | Jacober et al. |
| 6,685,678 B2 | 2/2004 | Evans et al. |
| 6,892,941 B2 | 5/2005 | Rosenblum |
| 7,006,894 B2 | 2/2006 | de la Huerga |
| 7,170,823 B2 | 1/2007 | Fabricius et al. |
| 7,253,411 B2 | 8/2007 | Kaushal et al. |
| 7,382,263 B2 | 6/2008 | Danowski et al. |
| 7,395,214 B2 | 7/2008 | Shillingburg |
| 7,471,993 B2 | 12/2008 | Rosenblum |
| 7,715,277 B2 | 5/2010 | de la Huerga |
| 7,755,478 B2 | 7/2010 | Niemiec et al. |
| 7,774,097 B2 | 8/2010 | Rosenblum |
| 7,844,361 B2 | 11/2010 | Jean-Pierre |
| 7,944,342 B2 | 5/2011 | Sekura |
| 7,978,564 B2 | 7/2011 | De La Huerga |
| 8,014,232 B2 | 9/2011 | Niemiec et al. |
| 8,019,471 B2 | 9/2011 | Bogash et al. |
| 8,116,907 B2 | 2/2012 | Hyde et al. |
| 8,212,677 B2 | 7/2012 | Ferguson |
| 8,391,104 B2 | 3/2013 | de la Huerga |
| 8,887,603 B2 | 11/2014 | Mitani et al. |
| 2001/0002448 A1 | 5/2001 | Wilson et al. |
| 2002/0032582 A1 | 3/2002 | Feeney, Jr. et al. |
| 2004/0054436 A1 | 3/2004 | Haitin et al. |
| 2006/0150817 A1* | 7/2006 | DeGuiseppi et al. ........... 96/108 |
| 2007/0023940 A1 | 2/2007 | Siess |
| 2007/0163917 A1* | 7/2007 | Friesen et al. ................ 206/528 |
| 2008/0164275 A1* | 7/2008 | Poutiatine et al. .............. 221/15 |
| 2008/0300719 A1 | 12/2008 | Duke |
| 2009/0069742 A1 | 3/2009 | Larsen |
| 2009/0134181 A1 | 5/2009 | Wachman et al. |
| 2009/0182582 A1 | 7/2009 | Hammon |
| 2009/0188386 A1 | 7/2009 | Beatty et al. |
| 2009/0192648 A1 | 7/2009 | Namineni et al. |
| 2009/0299522 A1 | 12/2009 | Savir et al. |
| 2010/0076595 A1 | 3/2010 | Nguyen |
| 2011/0060448 A1 | 3/2011 | Gotou et al. |
| 2011/0160896 A1 | 6/2011 | Kim |
| 2011/0251850 A1 | 10/2011 | Stephens |
| 2011/0279271 A1* | 11/2011 | Monroe ..................... 340/568.1 |
| 2012/0006708 A1 | 1/2012 | Mazur |
| 2012/0323360 A1 | 12/2012 | Lavin |
| 2013/0006652 A1 | 1/2013 | Vahlberg et al. |
| 2013/0036909 A1* | 2/2013 | Menard et al. .................... 95/91 |
| 2013/0114163 A1* | 5/2013 | Brown ............................ 96/118 |
| 2013/0146052 A1* | 6/2013 | Ding et al. ......................... 96/4 |
| 2014/0165827 A1* | 6/2014 | Gaikwad et al. ................. 95/25 |
| 2015/0090733 A1 | 4/2015 | Park |

\* cited by examiner

FUNCTIONAL DESICCANTS

RELATED APPLICATIONS

This application claims the benefit under 35 U.S.C. §119(e) of U.S. Provisional Application No. 61/800,973 filed on Mar. 15, 2013, the entire content of which is hereby incorporated by reference.

FIELD OF THE INVENTION

This document generally relates to functional desiccants, and more specifically to devices, systems, and methods relating to a desiccant package having enhanced monitoring capabilities and other functionality.

BACKGROUND

In general, a desiccant is a hygroscopic substance that induces or sustains a state of dryness (desiccation) in its vicinity. For example, pre-packaged desiccants are commonly encountered in containers of consumables (e.g., pill bottles), where the pre-packaged desiccants generally include a package of solids that absorb water. Although desiccants may come in many other forms, and may work through other principles, they generally do not provide any functionality other than absorbing moisture.

There remains a need for functional desiccants having enhanced monitoring capabilities and other functionality.

SUMMARY

A desiccant may be improved by including packaging with processing circuitry that may enable the desiccant to perform functions. The functions may include, without limitation, detecting contents of a container, sensing environmental conditions, storing a unique identifier, communication-related functionality, controlling operation of the desiccant, detecting the status of contents of a container, transmitting data, altering contents of a container, providing a signal in response to a condition, and so on.

In one aspect, a device includes a desiccant and an enclosure having an interior surrounding the desiccant. The enclosure may include a moisture vapor permeable membrane with a moisture permeability sufficient to pass moisture from outside the enclosure to the desiccant. The device may further include a functional device within the enclosure having processing circuitry to perform at least one function associated with the desiccant.

In another aspect, a device includes a desiccant and an enclosure having an interior surrounding the desiccant. The enclosure may include a moisture vapor permeable membrane with a moisture permeability sufficient to pass moisture from outside the enclosure to the desiccant. The device may further include a functional device coupled to an exterior of the enclosure including processing circuitry to perform at least one function associated with the desiccant.

BRIEF DESCRIPTION OF THE DRAWINGS

The foregoing and other objects, features, and advantages of the devices, systems, and methods described herein will be apparent from the following description of particular embodiments thereof, as illustrated in the accompanying figures. The figures are not necessarily to scale, emphasis instead being placed upon illustrating the principles of the devices, systems, and methods described herein.

DETAILED DESCRIPTION

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "above," "below," and the like, are words of convenience and are not to be construed as limiting terms.

Described herein are functional desiccants, and more specifically devices, systems and methods relating to a desiccant package having enhanced capabilities for monitoring and other functions. In general, as used throughout this disclosure a "desiccant" refers to a substance that induces or sustains a state of dryness (desiccation) in its vicinity. Additionally, unless explicitly stated otherwise or clear from the text, the desiccants described herein may include any item, substance, package, container, additive, and the like, as well as combinations of the foregoing, which may be included within a container or the like for desiccation.

Figure 1:
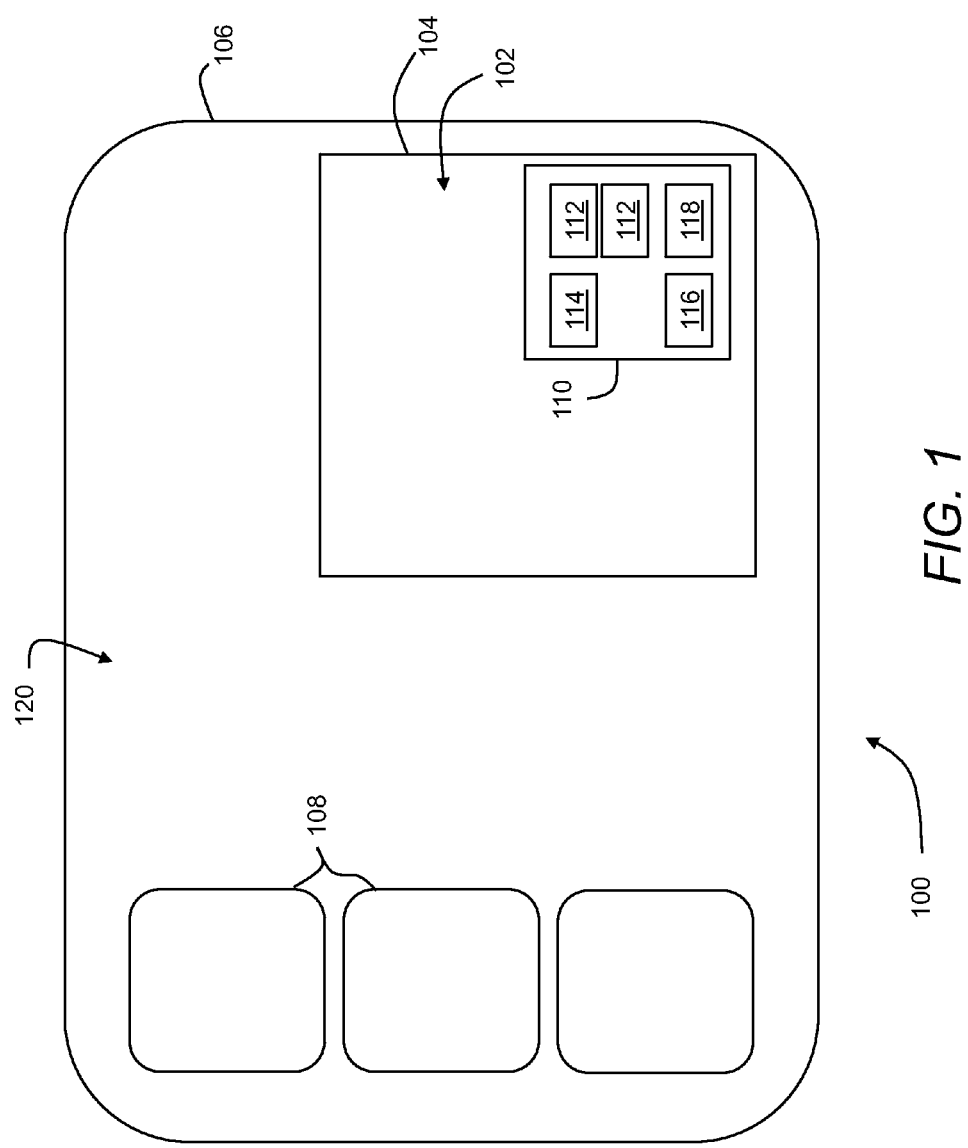
FIG. 1 shows a functional desiccant system.

FIG. 1 shows a functional desiccant system. The system 100 may include any device or system that would benefit from a functional desiccant having the capabilities described herein. This may for example include a package or container of consumables such as food, candy, medicine, nutritional supplements, vitamins, or the like. The package may also or instead include any other item or combination of items such as electronics, clothing, industrial chemicals, or any other items sensitive to humidity. The system 100 may include a desiccant 102, an enclosure 104 for the desiccant 102, and a functional device 110 within the enclosure 104. All of these components may be included in a container 106 that includes items 108.

The desiccant 102 may include a chemically stable or chemically inert substance, including, without limitation, silica, activated charcoal, calcium sulfate, calcium chloride, molecular sieves (e.g., zeolites), propylene glycol (e.g., E1520), hexylene glycol, butylene glycol, glyceryl triacetate (e.g., E1518), vinyl alcohol, neoagarobiose, sugar polyols such as glycerol, sorbitol (e.g., E420), xylitol and maltitol (e.g., E965), polymeric polyols like polydextrose (e.g., E1200), quillaia (e.g., E999), glycerin, alpha hydroxy acids, and so forth. For example, the desiccant 102 may include a pre-packaged desiccant, which may be a solid that absorbs water surrounded by a packaging, housing, enclosure, or the like. The desiccant 102 described herein may also or instead include desiccants for specialized purposes, which may be in forms other than solid, and may work through other principles, such as the chemical bonding of water molecules. The desiccant 102 may be part of a functional desiccant component that performs functions beyond desiccation, including, but not limited to, communication with other devices (e.g., via short or long range communication technologies embedded within the functional desiccant component) and consumable volume detection (e.g., via capacitance fields, strain gauges, optical/visual detection and analysis, or any other suitable techniques).

The enclosure 104 may include any suitable structure, membrane, or the like that permits the desiccant 102 to interact with the surrounding environment in a manner that supports the desired desiccant effect (e.g., for humidity control). The enclosure 104 may include a membrane surrounding the desiccant 102 to form a desiccant package, where the enclosure 104 completely or partially surrounds the desiccant 102. The membrane may be a moisture vapor permeable membrane or any other material with suitable vapor and moisture characteristics. The moisture vapor permeable membrane may include a moisture permeability sufficient to pass moisture from outside the enclosure 104 to the desiccant 102. The enclosure 104 may include the functional device 110 within the enclosure 104, coupled to the enclosure 104 (e.g., at least partially on an outside portion or an inside portion), or surrounded by the enclosure 104 (e.g., housed within the desiccant package).

The container 106 may be any type of container known in the art for housing items 108 (e.g., temporarily or permanently). The container 106 may, for example, be an environmentally sealed container to control humidity of air around one or more items 108 in the container 106. The container 106 may be a container for consumable items will be understood to similarly teach a container for dispensable items (e.g., in bulk or unit form), a container for ingestible items, a container for disposable items, and so on. The container 106 may be a cartridge for dispensing consumables such as a single-dose or single-unit dispensing container, a multi-dose, or multi-unit dispensing container. The container 106 may also or instead be a bottle such as a pill bottle, a medicine bottle, or any other similar packaging. The container 106 may be fully disposable, partially disposable, or fully reusable. The container 106 may include additional packaging materials along with the desiccant 102 and the items 108, such as plastic pellets, cotton wool, or the like to protect the items 108 from physical wear or damage, as well as tamperproof mechanisms such as an aluminum foil or other seal. The container 106 may include a reservoir 120 that holds any category of items 108, including, without limitation, unit-form or continuous-form consumables. The container 106 may also be a bag or other flexible or malleable container such as a re-sealable bag.

The items 108 may include dispensables. The term "dispensable" and related terms such as "dispensable unit" or just "unit" are intended to refer broadly to an item, combination of items, composition, component, material, compound or the like that can be dispensed in unit or continuous form, including without limitation consumables.

While a "dispensable" may be any item that can be dispensed, the term "consumable" or "consumable unit" is intended to refer to dispensables that are intended to be consumed by a user. Consumables are intended to include a wide array of ingestible consumable items and form factors for same. For example, consumable units may include one or more of pills, capsules, tablets, chewables, lozenges, dissolvables, sprinkles, dissolve-in-mouth micro-capsules, orally disintegrating tablets, chewable tablets (including jelly beans, gummies, and the like), gums, and so forth, as well as continuous form consumables such as liquids or powders, solutions, pastes, and suspensions, and combinations thereof. The consumables may also or instead include items provided as free powders, powder sachets, liquids, liquid sachets, vials, cups, cases, other storage forms, and so forth. More generally, the consumable units may be any composition for consumption in bulk, individual, individual pre-packaged, group pre-packaged and/or mixed item package form. For bulk form compositions, the "consumable unit" may be a predetermined portion for dispensing such as a teaspoon of liquid, a number of pills, a milligram of powder or the like, or a similar predetermined portion for dispensing or mixing into a compound locally created for dispensing prior to or after dispensing.

Similarly, the content of each consumable unit may vary significantly and may include but are not limited to prescription medication, non-prescription or over-the-counter medication, nutritional supplements, vitamin supplements, mineral supplements, veterinary medications, veterinary nutritional supplements, and so forth. Consumable units may also or instead include food and other items such as sugar, seeds, candies, snacks, pet treats, or other foods and the like, as well as any other pharmaceuticals, neutraceuticals, or other consumable items not identified above. These consumables that are intended to be ingestible are also referred to herein as "ingestibles" or "ingestible units."

While consumables may include items for consumption in the convention sense of ingestion as described above, consumables may also or instead include disposable items or the like that are intended for one time use. Thus, as used herein a "disposable" may be any consumable intended for a use other than ingestion. This may, for example, include disposable medical items such as dressings, bandages, Band-Aids, gauze, syringes, thermometers, individually packaged units of antibacterials and the like, as well as other items such as hearing aids, contact lenses and so forth that can be dispensed in individual units for one time use. This may also or instead include continuous form items not intended for ingestion including personal care items such as toothpaste, toothpicks, soap, sanitizer, moisturizer, cotton swabs and the like, as well as other household items such as glue, batteries, latex gloves, and so forth. All such disposables may be a form of consumable as those terms are used herein, and consumables may similarly be a form of dispensable.

It will be understood that while the foregoing terms (dispensable, consumable, ingestible, disposable) may be variously used in this disclosure to describe embodiments of the invention, the inventive concept generally applies to any and all such dispensables, and any description of one type of dispensable will be understood to refer to all such dispensables except where specifically noted to the contrary. Thus, for example, a container for consumable items will be understood to similarly teach a container for dispensable items, a container for ingestible items, and a container for disposable items. As another example, a schedule for delivery of a medical prescription will be understood to similarly teach a schedule for delivery of any dispensable, ingestible, consumable, and disposable, with suitable modifications being readily apparent to one of ordinary skill in the art.

The functional device 110 may generally include one or more sensors 112 and processing circuitry 114 that collectively perform at least one function associated with the desiccant 102. The functional device 110 may also or instead support a wide range of augmented functions for the desiccant 102 and/or the items 108 in the container 106 with the desiccant 102. In one aspect, the functional device 110 may detect contents of the container 106 holding the enclosure 104, such as the item(s) 108. The functional device 110 may also or instead detect one or more environmental conditions, for example, temperature, humidity, pressure, or light exposure within the reservoir of the container 106, or in the environment around the container 106. Although illustrated as contained within the enclosure 104, it will be appreciated that the functional device 110 may be disposed within the enclosure 104 or coupled to an outside of the enclosure 104. The functional device 110 may also or instead be disposed within the container 106 or on an outside surface of the container 106, and the sensor(s) 112 and processing circuitry 114 may be placed in different locations (e.g., with a sensor 112 outside the container 106 and the processing circuitry 114 inside the enclosure) and be coupled in a communicating relationship with one another to support augmented functions as contemplated herein.

The functional device 110 may include an identifier, e.g., stored in a memory of the processing circuitry 114, that uniquely identifies the item(s) 108, such as by recording the identifier when the enclosure 104 is placed in the container 106 with the item(s) 108. In this manner, the functional device 110 may store a unique identifier for the container 106 and/or contents of the container 106.

The functional device 110 may include a wireless communication system 116 for transmitting the identifier or other information (e.g., from the sensor(s) 112) to a remote location, which may be a location accessible through Radio-Frequency Identification (RFID) techniques, Near Field Communication (NFC) techniques, Bluetooth, Wi-Fi, or any other wireless communication protocol. The functional device 110 may include corresponding communications circuitry such as circuitry for NFC or Bluetooth communications. In another aspect, the functional device 110 may include an RFID tag. One of ordinary skill will understand that any of the above, or any item described with reference to the functional device 110, may be controlled by or be a part of the processing circuitry 114 of the functional device 110. For example, the processing circuitry may include or operate to control: a wireless communication system 116 configured to transmit the unique identifier to a remote location, an RFID tag, communications circuitry for one or more of near field communications and Bluetooth communications, a sensor 112 and communications circuitry (such as the wireless communication system 116 or any other suitable wired or wireless system), and the like. The processing circuitry 114 may also or instead include communications circuitry for one or more of short range wireless communications, low power wireless communications, and communications with a global positioning satellite. For example, a global positioning satellite system may be utilized to remotely track the desiccant 102, container 106, items 108, and so on.

The sensor(s) 116 may be include any suitable sensor or combination of sensors suitable for monitoring the desiccant 102, the items 108, the container 106, and so forth. This may for example include optical sensors, humidity sensors, or any of a variety of sensor systems to detect light, weight, pressure, temperature, humidity, vibration, and so forth. The sensor(s) 112 may be useful for detecting a status of the enclosure 104, the container 106, or item(s) 108 within the container 106 and providing status information corresponding to the status of the same. The wireless communication system 116 or other communications circuitry may be configured to transmit data obtained from the sensor.

In one aspect, the functional device 110 may be configured to transmit information, including, without limitation, status information relating to the item(s) 108, including, without limitation, information relating to environmental conditions. Thus, the functional device 110 may sense the item(s) 108 or a property thereof (e.g., with the sensor) and transmit a status accordingly. The functional device 110 may be configured to transmit information to any object, network, location, or person that might usefully receive such information.

The functional device 110 may be configured to augment operation of the desiccant 102 by controlling an interaction of the desiccant 102 with a surrounding environment (or any environment outside the enclosure 104). For example, the functional device 110 may control a physical exposure of the desiccant 102 to the surrounding environment, such as by mechanically exposing a solid-formed desiccant, or by mixing, stirring, or otherwise changing exposed surface areas of a loose form desiccant. In one aspect, the functional device 110 may detect a humidity in an area around the enclosure 104 and control the physical exposure of the desiccant 102 according to the humidity. In this manner, the functional device 110 may include a sensor 112 configured to detect humidity in an area around the enclosure 104 and a controller (which may be in the processing circuitry 114) configured to variably control a physical exposure of the desiccant 102 in response to a control signal. The processing circuitry 114 may be configured to adjust the control signal in response to the humidity so that the desiccant 102 is variably exposed to the reservoir 120 of the container 106 according to a detected humidity. In another aspect, the functional device 110 may detect one or more other conditions, either alone or in combination with the humidity, to control the physical exposure of the desiccant 102.

The functional device 110 may also or instead control the physical exposure of the desiccant 102 according to a predetermined schedule, such as by mixing the desiccant 102 at predetermined intervals or by progressively exposing more of a solid-form desiccant over time. The functional device 110 may control a temperature of the desiccant 102, an agitation of the desiccant 102, or any other property associated with the desiccant 102 that might affect characteristics (e.g., moisture transfer characteristics) of the desiccant 102.

In another aspect, the functional device 110 may be configured to augment handling of contents of a container 106 holding the enclosure 104. For example, the functional device 110 may be configured to alter the contents such as the item(s) 108 upon occurrence of a predetermined event. Altering the contents may include adding a destabilizing agent to the contents, adding a pigment to the contents, adding an odor to the contents, adding a toxin to the contents, adding a solvent to the contents, heating the contents, cooling the contents, igniting the contents, exploding the contents, otherwise tagging the contents using other tagging methods known by a skilled artisan, and so forth. More generally, the contents may be acted upon to render the contents unusable, to provide an indication of a change in state, or otherwise alter the contents in a desired manner. The predetermined event may be any suitable triggering event. For example, the predetermined event may include a passage of time, e.g., to an expiration date or the like. The predetermined event may include a failure to receive an authorization within a predetermined time. In such a configuration, the functional device 110 may be configured to receive and authenticate messages over a wireless network or the like that provides an external confirmation that the contents should remain in an active state. When such messages fail to arrive (e.g., a failure to receive an authorization) the functional device 110 may take appropriate action to alter the contents accordingly. In this manner, the contents of a container 106 may include a failsafe that prevents unauthorized transportation, opening, use, or other activity, or that renders the item(s) 108 unusable under predetermined conditions. The predetermined event may also or instead include receipt of a remote signal with an instruction to alter the contents. The predetermined event may also or instead include a movement of the device outside of a geofence. In this manner, contents of the container 106 may be subject to any desired geographic constraints.

The functional device 110 may include a signaling device 118. The signaling device 118 may provide one or more of an audible sound, a vibration, or an illumination. The signaling device may provide a signal in response to an internal condition, e.g., an internal condition of a container 106 holding the enclosure 104. For example, the internal condition may be an expiration of the contents of a container 106. The signaling device may provide a signal in response to an external condition, e.g., an external condition of the container 106. The external condition may include one or more of temperature, humidity, time, pressure, vibration, and the like. The external condition may be transmitted to the functional device 110 from a remote source. The signaling device 118 may also or instead couple to an external signaling device. For example, the signaling device 118 may send a signal to LEDs on the container 106. The signaling device 118 may also or instead provide a signal in response to an event relating to the contents of the container 106 (e.g., the items 108). For example, signaling device 118 may provide a signal if it receives an emergency signal (or the like) from a server, which may include a signal that the items 108 have been recalled, are deemed unacceptable, or the like.

In one aspect, the functional device 110 may be operable to maintain a unit count of items 108 within the container 106 using any suitable combination of sensors 112 and processing circuitry 114. An implementation may include calibration circuitry configured to adjust any data according to desiccant activity. For example, the calibration circuitry may be configured to adjust a consumable units count (e.g., item(s) 108 count) according to one or more of temperature, humidity, time, and desiccant activity. The desiccant activity may be provided by the functional device 110.

Figure 2:
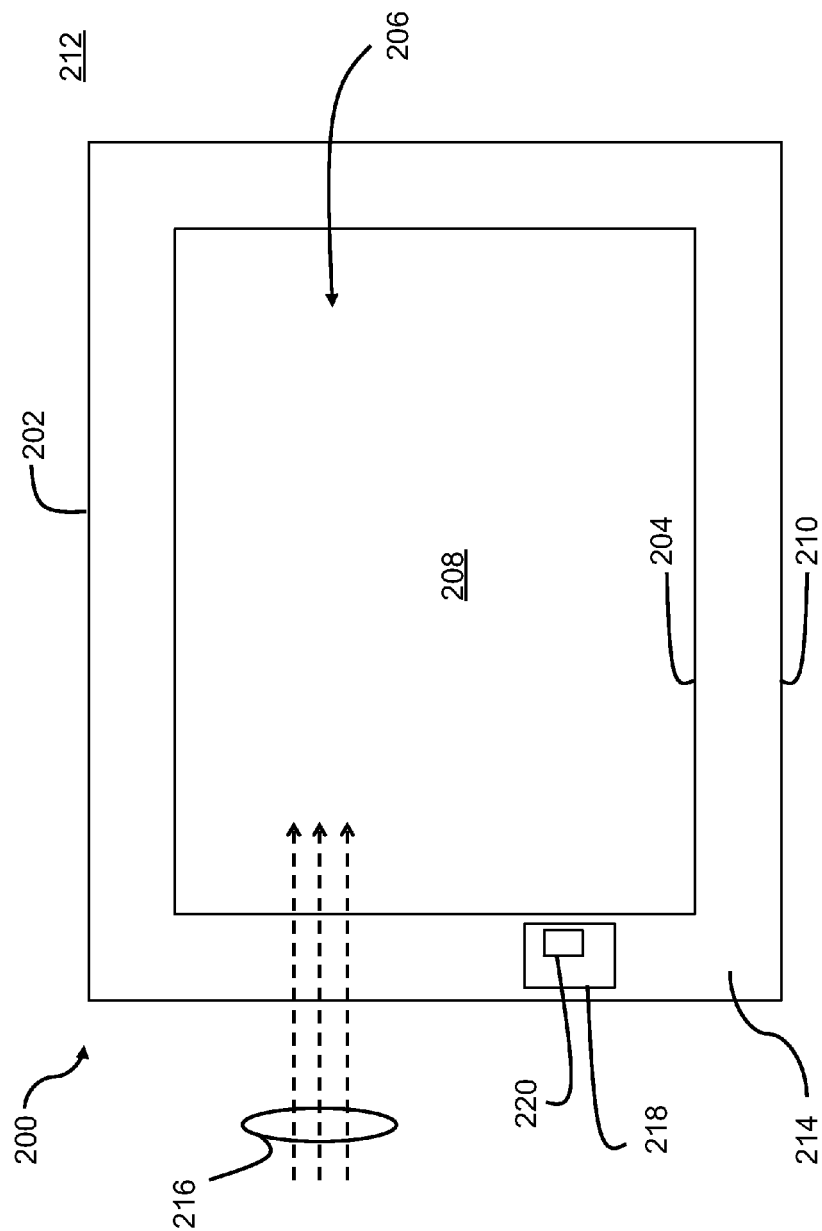
FIG. 2 shows a functional desiccant.

FIG. 2 shows a functional desiccant. A desiccant package 200 may include an enclosure 202 having an interior portion 204 surrounding a desiccant 206, with the desiccant 206 disposed in an interior 208 of the desiccant package 200. The enclosure 202 may further include an exterior portion 210 adjacent to the outside 212 of the desiccant package 200.

The desiccant package 200 may be any of the functional desiccants described herein, for example, a desiccant package for a container housing consumables or the like.

The enclosure 202 may include a membrane 214, which may be a moisture vapor permeable membrane. The moisture vapor permeable membrane may include moisture permeability sufficient to pass moisture from the outside 212 of the enclosure 202 to the desiccant 206 located on the interior 208 of the enclosure 202 (an example of a path taken by moisture vapor is indicated by the dashed arrows 216 in FIG. 2). As further shown in FIG. 2, the enclosure 202 may include a functional device 218.

The functional device 218 may be located within the enclosure 202 (as shown in FIG. 2), or it may be coupled to the exterior portion 210 or the interior portion 204 of the enclosure 202. In another aspect, the functional device 218 may be disposed within a wall of the enclosure 202, that is, neither inside nor outside the enclosure 202, but instead within the body of the enclosure 202 itself, or spanning from the inside to the outside of the enclosure. In this latter arrangement, the functional device 218 may usefully control a passage of air or humidity between the inside and outside, e.g., by selectively opening and closing or selectively exposing and covering a permeable or semi-permeable portion of the enclosure 202. The functional device 218 may include a component 220, which may be any of the components described herein, including, without limitation, processing circuitry (e.g., to perform at least one function associated with the desiccant 206), a sensor, a unique identifier, a controller, a signaling device, a tag, communications circuitry, a communications system, actuators to controllably expose the interior of the enclosure 202, and so on.

Figure 3:
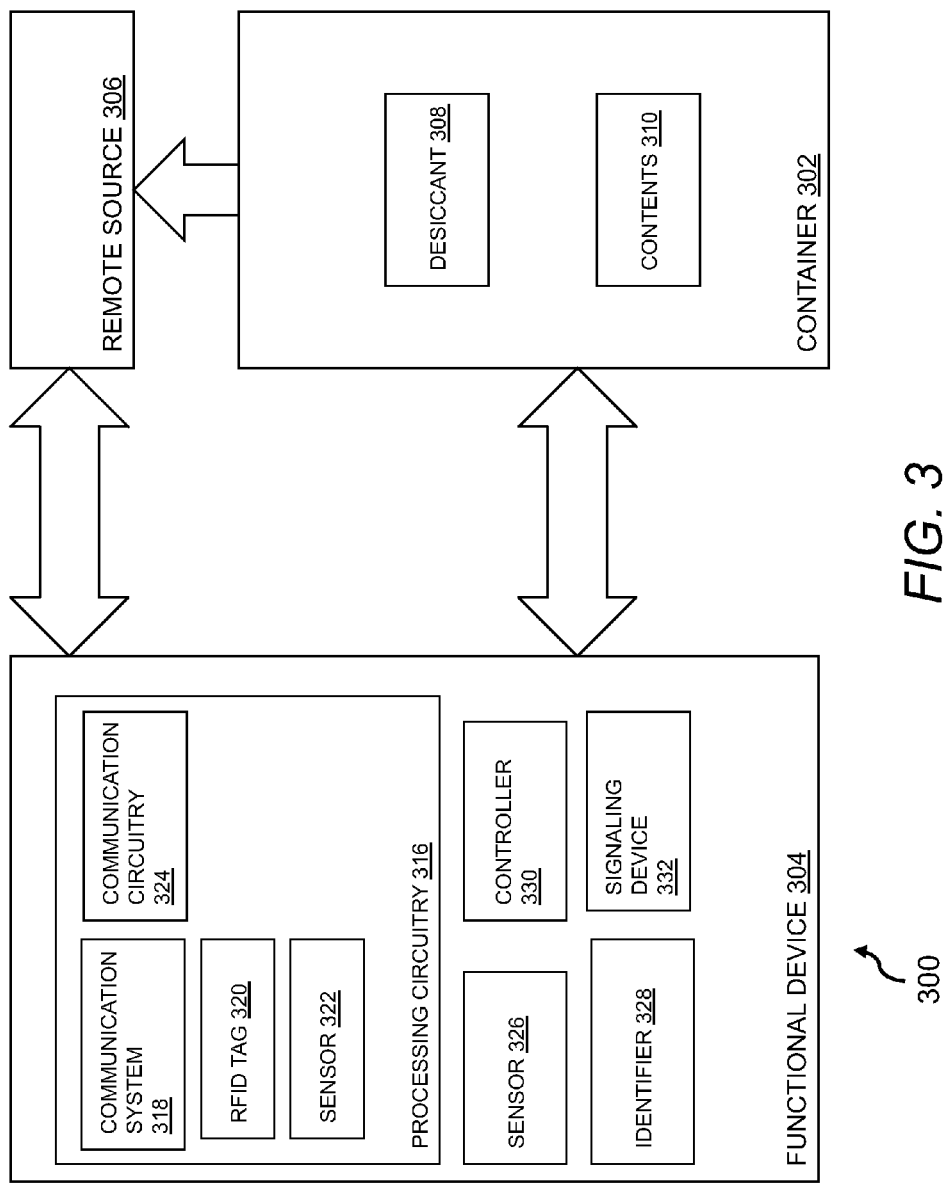
FIG. 3 is a block diagram of a functional desiccant system.

FIG. 3 is a block diagram of a functional desiccant system 300. The functional desiccant system 300 may generally include a container 302, a functional device 304, and a remote source 306, where these components may interact with one another (e.g., communicate, cooperate, engage, sense data, and so forth) as indicated by the arrows included in FIG. 3.

The container 302 may include a desiccant 308 and contents 310 (e.g., the items 108 referenced in FIG. 1). The desiccant 308 may be any desiccant referenced herein or otherwise known in the art (or that becomes known in the art). Similarly, the contents 310 may be any items referenced herein including, without limitation, consumables. The container 302 may be characterized by any number of conditions, for example, environmental conditions such as temperature, humidity, and the like, which may be detected by suitable sensors. The conditions may be used alone or in combination with other conditions by the functional desiccant system 300. The other conditions may include, without limitation, a status of the container 302 or contents 310, time or a time interval, location, proximity (e.g., to a beacon or other signal), and the like.

The functional device 304 may include processing circuitry 316 to perform at least one function associated with the desiccant 308 or container 302. The processing circuitry 316 may include one or more of a communications system 318, an RFID tag 320, a sensor 322, communications circuitry 324, and so forth. The functional device 304 may also include one or more of a sensor 326, an identifier 328, a controller 330, a signaling device 332, and so forth, where any or all of these components may be part of the processing circuitry 316 described above.

The remote source 306 may transmit remote signals to the functional device 304, which receives the remote signals. The remote signals may include external conditions, an authorization, and so forth. The functional device 304 may send signals to the remote source 306, e.g., through a signaling device 332. The remote source 306 may be located in a remote location. The remote source 306 may, for example, include a network resource remote from and coupled in a communicating relationship with the functional device 304, or the remote source 306 may include a local processing/communication resource that communicates through a local communication system with the functional device such as an RFID reader, WiFi network, and the like.

The communications system 318 may include a wireless communication system configured to transmit the identifier 328 to the remote source 306. In addition, or in the alternative, the communications system 318 may include type of communication system known by a skilled artisan that may be useful for the functional device 304 described herein.

The sensor 322, 326 may, for example, detect contents 310 of the container 302, one or more environmental conditions, one or more other conditions, and so on. The sensor 322, 326 may detect a condition of the container 302, for example, around the enclosure of the desiccant 308.

The communications circuitry 324 may be circuitry for one or more of Near Field Communications (NFC) and Bluetooth communications. The sensor 322 may work in conjunction with the communications circuitry 324. For example, the sensor 322 may detect the status of the contents 310 in the container 302 and provide status information corresponding to the status of the contents 310, for example, to the remote source 306. In this manner, the communications circuitry 324 may be configured to transmit data obtained from the sensor 322.

The identifier 328 may be a unique identifier that is stored in a memory of the functional device 304, in the container 302, or associated with the contents 310.

The functional desiccant system 300 may be configured such that the functional device 304 controls operation of the desiccant 308 by controlling an interaction of the desiccant 308 with an environment of the container 302. For example, the functional device 304 may control the physical exposure of the desiccant 308 to the environment outside of the enclosure of the desiccant 308 in the container 302. In this manner, the functional device 304 may include a sensor 322, 326 configured to detect an environmental condition and a controller 330 configured to variably control the physical exposure of the desiccant 308 in response to a control signal, where the processing circuitry 316 is configured to adjust the control signal in response to the environmental condition.

The controller 330 may be operable to control components of the functional desiccant system 300 (e.g., the container 302, functional device 304, and the remote source 306). The controller 330 may be electrically or otherwise coupled in a communicating relationship with the functional device 304, and the other various components of the devices and systems described herein. The controller 330 may include any combination of software and/or processing circuitry suitable for controlling the various components of the functional desiccant system 300 described herein including without limitation microprocessors, microcontrollers, application-specific integrated circuits, programmable gate arrays, and any other digital and/or analog components, as well as combinations of the foregoing, along with inputs and outputs for transceiving control signals, power signals, sensor signals, and so forth. In one aspect, this may include circuitry directly and physically associated with the container 302, the functional device 304, or the remote source 306, such as a processor. In another aspect, this may be a processor, which may be associated with a personal computer or other computing device coupled to the functional desiccant system 300, e.g., through a wired or wireless connection. Similarly, various functions described herein may be allocated between a controller, processor, and a separate computer. All such computing devices and environments are intended to fall within the meaning of the term "controller" or "processor" as used herein, unless a different meaning is explicitly provided or otherwise clear from the context.

The above systems, devices, methods, processes, and the like may be realized in hardware, software, or any combination of these suitable for the control, data acquisition, and data processing described herein. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same. In another aspect, means for performing the steps associated with the processes described above may include any of the hardware and/or software described above. All such permutations and combinations are intended to fall within the scope of the present disclosure.

It should further be appreciated that the methods above are provided by way of example. Absent an explicit indication to the contrary, the disclosed steps may be modified, supplemented, omitted, and/or re-ordered without departing from the scope of this disclosure.

The method steps of the invention(s) described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A device comprising:
    a desiccant;
    an enclosure having an interior surrounding the desiccant and including a moisture vapor permeable membrane with a moisture permeability sufficient to pass moisture from outside the enclosure to the desiccant; and
    a functional device within the enclosure including processing circuitry to perform at least one function associated with the desiccant, wherein the functional device is configured to control operation of the desiccant by controlling an interaction of the desiccant with an environment outside the enclosure, and wherein the functional device controls a physical exposure of the desiccant to the environment in a manner that varies over time.

2. The device of claim 1 wherein the functional device includes a sensor.

3. The device of claim 2 wherein the sensor detects contents of a container holding the enclosure.

4. The device of claim 2 wherein the sensor detects one or more environmental conditions.

5. The device of claim 1 wherein the functional device stores a unique identifier for the device.

6. The device of claim 5 wherein the processing circuitry includes a wireless communication system configured to transmit the unique identifier to a remote location.

7. The device of claim 1 wherein the processing circuitry includes an RFID tag.

8. The device of claim 1 wherein the processing circuitry includes communications circuitry for one or more of near field communications, short range wireless communications, low power wireless communications, and communications with a global positioning satellite.

9. The device of claim 1 wherein the processing circuitry includes a sensor and communications circuitry.

10. The device of claim 9 wherein the sensor is configured to detect a status of an item and provide status information corresponding to the status of the item.

11. The device of claim 9 wherein the sensor is configured to detect a condition of an environment around the enclosure.

12. The device of claim 11 wherein the condition is one or more of a humidity and a temperature.

13. The device of claim 9 wherein the communications circuitry is configured to transmit data obtained from the sensor.

14. The device of claim 1 wherein the functional device includes a sensor configured to detect a humidity in an area around the enclosure and a controller configured to variably control the physical exposure of the desiccant in response to a control signal, the processing circuitry configured to adjust the control signal in response to the humidity.

15. The device of claim 14 wherein the functional device detects one or more other conditions for use in combination with the humidity to adjust the control signal.

16. The device of claim 1 wherein the functional device controls the physical exposure of the desiccant according to a predetermined schedule.

17. The device of claim 1 wherein the functional device controls a temperature of the desiccant or an agitation of the desiccant.

18. The device of claim 1 wherein the processing circuitry of the functional device is configured to alter contents of a container holding the enclosure upon occurrence of a predetermined event.

19. The device of claim 18 wherein altering the contents includes one or more of adding a destabilizing agent to the contents, adding a pigment to the contents, adding an odor to the contents, adding a toxin to the contents, adding a solvent to the contents, and heating the contents.

20. The device of claim 18 wherein the predetermined event includes a passage of time.

21. The device of claim 18 wherein the predetermined event includes a failure to receive an authorization within a predetermined time.

22. The device of claim 18 wherein the predetermined event includes receipt of a remote signal.

23. The device of claim 18 wherein the predetermined event includes a movement of the device outside a geofence.

24. The device of claim 1 wherein the functional device includes a signaling device.

25. The device of claim 24 wherein the signaling device provides one or more of an audible sound, a vibration, or an illumination.

26. The device of claim 25 wherein the signaling device provides a signal in response to an internal condition of a container holding the enclosure.

27. The device of claim 26 wherein the internal condition is an expiration of contents of the container.

28. The device of claim 24 wherein the signaling device provides a signal in response to an external condition of a container holding the enclosure.

29. The device of claim 28 wherein the external condition includes one or more of temperature, humidity, time, pressure, and vibration.

30. The device of claim 28 wherein the external condition is transmitted to the functional device from a remote source.

31. A device comprising:
    a desiccant;
    an enclosure having an interior surrounding the desiccant and including a moisture vapor permeable membrane with a moisture permeability sufficient to pass moisture from outside the enclosure to the desiccant; and
    a functional device coupled to an exterior of the enclosure including processing circuitry to perform at least one function associated with the desiccant, wherein the functional device is configured to control operation of the desiccant by controlling an interaction of the desiccant with an environment outside the enclosure, and wherein the functional device controls a physical exposure of the desiccant to the environment in a manner that varies over time.

* * * * *